US012678209B2

(12) United States Patent
Chu et al.

(10) Patent No.: US 12,678,209 B2
(45) Date of Patent: Jul. 14, 2026

(54) METHOD AND APPARATUS FOR REGULATING AND CONTROLLING POLY-METHYLMETHACRYLATE INJECTION BY USING PRESSURE

(71) Applicant: Unitron Medical INC., New Taipei City (TW)

(72) Inventors: Woei-Chyn Chu, Taipei (TW); Yin-Jiun Tseng, New Taipei City (TW); William Chu, New Taipei City (TW)

(73) Assignee: Unitron Medical INC., New Taipei City (TW)

( * ) Notice: Subject to any disclaimer, the term of this patent is extended or adjusted under 35 U.S.C. 154(b) by 103 days.

(21) Appl. No.: 18/293,551

(22) PCT Filed: Aug. 1, 2022

(86) PCT No.: PCT/CN2022/109492
§ 371 (c)(1),
(2) Date: Jan. 30, 2024

(87) PCT Pub. No.: WO2023/006114
PCT Pub. Date: Feb. 2, 2023

(65) Prior Publication Data
US 2024/0335220 A1     Oct. 10, 2024

Related U.S. Application Data

(60) Provisional application No. 63/227,399, filed on Jul. 30, 2021.

(51) Int. Cl.
*A61B 17/88* (2006.01)
*A61B 90/00* (2016.01)

*G16H 40/63* (2018.01)
*A61B 17/00* (2006.01)

(52) U.S. Cl.
CPC .......... *A61B 17/8822* (2013.01); *A61B 90/06* (2016.02); *G16H 40/63* (2018.01); *A61B 2017/00022* (2013.01); *A61B 2090/064* (2016.02)

(58) Field of Classification Search
CPC .................................. A61B 17/8802–17/8847
See application file for complete search history.

(56) References Cited

U.S. PATENT DOCUMENTS

| | | | | |
|---|---|---|---|---|
| 11,534,220 | B2 * | 12/2022 | Chu .................. | A61M 5/16877 |
| 2007/0299450 | A1 * | 12/2007 | Her .................... | A61B 17/8822 |
| | | | | 606/279 |
| 2009/0131945 | A1 * | 5/2009 | Liu ..................... | A61B 17/8827 |
| | | | | 606/92 |
| 2011/0160737 | A1 * | 6/2011 | Steffen ............... | A61B 17/8822 |
| | | | | 606/94 |
| 2017/0296247 | A1 * | 10/2017 | Hsueh ................ | A61B 17/8825 |
| 2020/0383715 | A1 * | 12/2020 | Chu ....................... | A61M 31/00 |

* cited by examiner

*Primary Examiner* — Zade Coley
(74) *Attorney, Agent, or Firm* — MUNCY, GEISSLER, OLDS & LOWE, P.C.

(57) ABSTRACT

The present invention provides a pressure-guided bone cement injection method and device, comprising an algorithm capable of sensing at least one environmental parameter. It dynamically monitors saturation level of bone cement within the vertebral body of a patient in real-time and actively provides feedback to the device to modify injection conditions.

5 Claims, 5 Drawing Sheets

METHOD AND APPARATUS FOR REGULATING AND CONTROLLING POLY-METHYLMETHACRYLATE INJECTION BY USING PRESSURE

BACKGROUND OF THE INVENTION

Technical Field of the Invention

This invention provides a method for injecting bone cement into the vertebral body, particularly a method that utilizes algorithms to control pressure output values for guiding the injection of bone cement.

Background

Since the late twentieth century, the use of bone cement in treating patients with vertebral vascular malformations has increased significantly, highlighting the growing importance of bone fillers in orthopedic treatment. Particularly noteworthy is the application of bone fillers in the treatment of vertebral support and shaping to prevent compression of spinal nerves, offering an alternative to traditional neuro-decompression surgeries or a combination of conventional spinal fixation procedures to address nerve compression. Minimally invasive vertebral shaping surgery is performed percutaneously within the vertebrae, involving the placement of artificial bone cement (Poly-methylmethacrylate, PMMA) or other bone filling materials into the damaged vertebrae. This enhances vertebral strength and stability, reducing chronic pain caused by vertebral damage. To facilitate the smooth insertion of bone fillers into the damaged vertebrae, the implantation instrument for bone fillers becomes crucial. The stability of injection rate, applied force, convenience, adaptability in conjunction with other instruments, all intricately relate to the case of operation and impact the surgical outcome.

The majority of existing devices for bone cement injection utilize syringes or specially designed injectors to deliver bone cement into the fractured vertebral body. However, situations may arise where bone cement leaks outside the vertebral body due to factors such as osteoporosis, fractures, or excessive injection pressure applied by the operator, potentially leading to safety concerns.

The primary challenge faced during bone cement injection is the situation of overflow occurring throughout the injection process. "Decompressed percutaneous vertebroplasty: A secured bone cement delivery procedure for vertebral augmentation in osteoporotic compression fractures" (JINJ-5173; No. of Page 6) discloses a bone cement injection method that applies a constant continuous suction pressure to the opposite side of the vertebral body during cement injection to reduce the probability of leakage during the bone cement injection process. This can be considered as a safer and more effective choice for bone cement injection. However, the injection method can only address blockage or overflow situations that may occur during the bone cement injection process, relying on the physician's experience to control the injection condition. For example, as bone cement gradually fills the interior of the vertebral body, continuous injection of bone cement may pose a risk of leakage into the surrounding cavity or veins, leading to leakage during the bone cement injection process and causing complications such as nerve compression or pulmonary embolism for the patient.

Therefore, providing a safe and effective bone cement injection method that can overcome the potential occurrence of overflow during the injection process has become a critical issue that the relevant industry urgently needs to address.

SUMMARY OF INVENTION

Accordingly, in one aspect, the invention is to provide an algorithm-controlled pressure-guided bone cement injection method. Through this method, the real-time assessment of the vertebral body bone cement injection status in patients is achievable, allowing for timely adjustments to injection parameters, modes, or cessation of bone cement injection.

In another aspect, the invention is to provide an algorithm-controlled pressure-guided bone cement injection method that can dynamically assess the saturation level of bone cement injected into the vertebral body of a patient, serving as a reference or basis for injection conditions.

In another aspect, the invention is to provide an algorithm-controlled pressure-guided bone cement injection method that employs embedded algorithms within the pressure unit to calculate pressure output values for injecting bone cement into the vertebral body.

In a further aspect, the invention is to provide an algorithm-controlled pressure-guided bone cement injection method that utilizes sensing unit to measure pressure changes within the vertebral body, calculating the saturation level of bone cement injection as a reference or basis for adjusting injection conditions.

In a still further aspect, the invention is to provide an algorithm-controlled pressure-guided bone cement injection method that, through the injection device, reduces the occurrence of overflow during vertebral bone cement injection surgeries.

To achieve these objectives, the invention discloses a method for algorithm-controlled pressure-guided bone cement injection, comprising the following steps: setting an initial pressure output value, sensing at least one environmental parameter, calculating the rate of pressure change within the vertebral body based on environmental parameters, determining if the pressure change rate is less than a pressure change threshold, calculating the saturation level of bone cement within the vertebral body, deciding to increase the pressure output value or stop the operation of the bone cement injection device. As the pressure output value is increased, some bone cement will be drawn out of the vertebral body, leaving a small portion in a laminar flow mode adhering to the inner wall of the vertebral body. Over time, the bone cement will gradually fill the vertebral body.

The invention also provides a device for algorithm-controlled pressure-guided bone cement injection, comprising a pressure unit, a propulsion unit, a control unit, and a sensing unit. The pressure unit provides suction pressure, the propulsion unit delivers bone cement into the vertebral body, the sensing unit detects at least one environmental parameter, and the control unit comprising an algorithm module, wherein the algorithm module can control the pressure unit based on the calculation results.

In one embodiment of the invention, the environmental parameter comprises at least one of the pressure values within the propulsion unit, the pressure value within the pressure unit, and the pressure value within the vertebral body.

To provide the examiner with a more detailed understanding and recognition of the features and achieved effects of the present invention, a detailed description, accompanied by preferred embodiments, is hereby provided. In the present invention, addressing the limitation of existing bone cement injection devices in responding to the unknown filling status of bone cement within the vertebral body, leading to bone cement leakage and affecting patient safety, a novel algorithm for controlling pressure-guided bone cement injection is proposed. This method allows real-time calculation of the bone cement injection status within the patient's vertebral body and provides feedback signals to the control unit, thereby achieving the purpose of real-time feedback control.

The algorithm-controlled pressure-guided bone cement injection method provided by the present invention can uniformly fill the entire affected area during the bone cement injection process through pressure guidance, thereby reducing the risk of bone cement leakage.

Therefore, the present invention provides a novel algorithm-controlled pressure-guided bone cement injection method. It involves sensing at least one environmental parameter and transmitting the at least one environmental parameter to the control unit. On the other hand, it further controls the injection of bone cement into the vertebral body through algorithmic computations.

In accordance with the above principles, further explanations are provided below regarding the components, characteristics, their combinations, and their interactive relationships involved in the algorithm-controlled pressure-guided bone cement injection method and device provided by the present invention. Referring to FIG. 1, it illustrates a block diagram of a system for the algorithm-controlled pressure-guided bone cement injection device provided by the present invention, according to a preferred embodiment. As shown, the algorithm-controlled pressure-guided bone cement injection device 10 for provided by the present invention comprises a pressure unit 11, a propulsion unit 12, a control unit 13, and at least one sensing unit 14. The control unit 13 comprises an algorithm module 131 and connects to the pressure unit 11 and the propulsion unit 12. When the control unit 13 obtains at least one sensing parameter from the at least one sensing unit 14, the algorithm module 131 of the control unit 13 calculates the required pressure output value and controls the injection conditions of bone cement by the pressure unit 11.

The present invention provides an algorithm-controlled pressure-guided bone cement injection method. When the at least one sensing unit 14, positioned at any location on the pressure unit 11, detects at least one environmental parameter, transmits the at least one environmental parameter to the control unit 13. Subsequently, the algorithm module 131 of the control unit 13 processes the content of the at least one environmental parameter, compares it with pre-set ideal values, and uses the resulting differential value as a reference to control the pressure output value provided by the pressure unit 11. This establishes a self-feedback system mechanism. Through the self-feedback system mechanism, the algorithm-controlled pressure-guided bone cement injection device 10 for provided by the present invention offers a convenient operating mode. Compared to the current situation where the operator relies solely on the sense of touch for judging and controlling pressure output value, this system provides higher operational stability and more accurate and consistent operational responses.

Building upon the embodiment described above, the present invention provides an algorithm-controlled pressure-guided bone cement injection device 10. The user or the control unit 13 can more accurately understand operational conditions, environmental status, and real-time changes in pressure output value of the pressure unit 11 from the observation results of the at least one sensing unit 14.

Furthermore, by indirectly obtaining information, the delivery status of bone cement by the propulsion unit 12 can be inferred, and corresponding adjustments to pressure output value can be made. Compared to other types of bone cement injectors in the prior art, including bone cement injection systems with pressure guidance but lacking sensing devices, the pressure-guided bone cement injection method provided by the present invention allows for more precise control during the injection process. It enables adjustments based on the impact of the pressure provided to the injection target area, making the injection process smoother and avoiding the high risk of leakage due to inappropriate pressure application. Additionally, the sensing and adjustment of pressure intensity indirectly influence the parameters of bone cement injection, allowing for relatively fine adjustments even with significant changes. On the other hand, when the sensing position is far from the actual injection end of bone cement, environmental parameter changes are relatively simple, and the obtained measurement values are more accurate. Therefore, more accurate feedback values can be obtained for pressure output value adjustments, enhancing the convenience of the injection system's operation.

Specifically, the bone cement injection method provided by the present invention is designed to address challenges associated with the gradual solidification of bone cement material during the injection process. As a result, it is not feasible to place pressure sensors inside the bone cement injector. In a preferred embodiment of the present invention, the sensing unit 14 is positioned between the propulsion unit 12 and the bone cement injection device 10. In this arrangement, if the pressure inside the bone cement injection device 10 increases, the resistance increases, causing the force applied by the propulsion unit to rise. This results in an increase in pressure sensed by the pressure sensor, providing an estimate of the bone cement injection pressure. This method involves monitoring initial pressure values, intermediate pressure values, and maximum pressure values. Through the algorithm module's calculation and feedback control mechanism, in the repetitive process of continuous injection and solidification of bone cement, the method accurately assesses the rate of pressure increase and saturation level in the injection target area. This enables effective evaluation and feedback on the amount of bone cement injected into the target area and when to stop the injection. The described approach effectively avoids the high risk of leakage due to inappropriate pressure application. Furthermore, as bone cement may solidify during the suction process within the vertebral body or between the pipelines, knowing the pressure difference applied to the ends of the vertebral body is crucial. The sensing unit 14 positioned on the pressure unit 11 provides distinct sensing data, offering higher detection accuracy compared to prior arts. Based on the aforementioned information, the at least one sensing unit 14 in the present invention senses at least one environmental parameter, including the pressure within the target site.

Refer to FIG. 2 of the drawings associated with the present invention, illustrating another preferred embodiment of the algorithm-controlled pressure-guided bone cement injection method. When clinicians commence treatment, they can pre-set variable initial pressure output values in the control unit 13. Subsequently, the sensing unit 14 monitors the pressure values of the pressure unit 11. As the propulsion unit 12 begins to inject bone cement, the algorithm module 131 calculates the rate of pressure change. After a certain measurement period and assessment, the algorithm commands the pressure unit 11 to increase the pressure output value until the intermediate pressure output value reaches the maximum output value, at which point the device stops injecting bone cement. Taking FIG. 2 as an example, the initial pressure output value can be set to 400 mmHg. When the pressure is measured at 400 mmHg and the bone cement cannot be moved, the algorithm increases the intermediate pressure output value to 500 mmHg. The pressure output value is then increased to 500 mmHg, and so on, until it reaches the maximum output value. In this example, the maximum output value is 680 mmHg. The algorithm determines to stop injecting bone cement at this point.

FIG. 3 illustrates a detailed example of the control algorithm S101, where the algorithm module 131 includes an exemplary pressure control algorithm S101. As described, the pressure control algorithm S101 involves monitoring certain parameters (such as pressure change rate and saturation level of bone cement within the vertebral body). These parameters can be continuously or periodically monitored. The pressure control algorithm S101 examines the monitored parameters against predefined parameter profiles to determine whether individual or combined parameters fall within the specified range of the predefined parameter profiles. If the monitored parameters fall within the specified range of the predefined parameter profiles, the command to output pressure can continue the injection of bone cement. If the monitored parameters are outside the specified range of the predefined parameter profiles, the algorithm 131 adjusts the command for pressure output accordingly or terminates the pressure output. The following is a non-exhaustive list of situations in which the algorithm 131 may adjust, terminate, or interrupt the command for pressure output:

(1) The measured pressure change rate exceeds the default pressure change threshold.

(2) The output pressure value exceeds the maximum pressure output value.

(3) The pressure change rate is less than the default pressure change threshold.

(4) The bone cement within the vertebral body approaches saturation.

In the algorithm flowchart, the process blocks are as follows:

S102: Set a variable initial pressure output value in the control unit 13; the initial pressure value can be manually set, for example, to 400 mmHg.

S104: Calculate the saturation range of bone cement within the vertebral body; subtract the pressure output value from the pressure output value multiplied by a parameter, where the parameter can be manually set.

S106: Monitor or read the pressure value of the pressure unit 11 through sensing unit 14.

S108: Initiate the injection of bone cement into the vertebral body using the propulsion unit 12.

S110: Calculate the pressure change rate using a differential or derivative method.

S112: Compare the pressure change rate with the pressure change threshold and calculate the saturation level of bone cement; use the monitored pressure value divided by the pressure output value to calculate the saturation level.

If the pressure change rate is less than the pressure change threshold, proceed to S114: Command the control system 13 to increase the pressure output value; in this example, increase the initial pressure value from 400 mmHg to an intermediate pressure value of 500 mmHg.

S116: Compare the pressure value with the saturation range of bone cement; if the pressure value is less than the saturation range of bone cement, return to S106: re-monitor the pressure value, then repeat the process from S102 to S116, until the pressure value reaches the maximum output value; in this example, 680 mmHg.

If, during S116, the pressure value is greater than the saturation range of bone cement, proceed to S118.

S118: Command the propulsion unit 12 to stop injecting bone cement.

For instance, when the pressure continuously rises during the injection process, reaching the injection measurement threshold due to the cavity being filled, it indicates that the filling of bone cement at the operational site has been completed. Alternatively, if there is a blockage in the operational environment, unsuitable for bone cement injection, connecting the pressure unit would result in a rapidly measured pressure change, indicating an unsuitable operational state. Therefore, through the aforementioned design, a bone cement injection system is obtained with a feedback mechanism that provides real-time and rapid feedback during the operational process, offering excellent feedback on how the system chooses to initiate and complete operations.

In the embodiments described above, the at least one environmental parameter provided by the present invention includes the pressure within the propulsion unit, the pressure within the pressure unit, or the pressure at the target site.

In summary, the present invention indeed provides a system for algorithm-controlled pressure-guided bone cement injection. This system can dynamically observe environmental parameters within the operating system, including the pressure at the application site of the pressure-guided bone cement injection device. The observed data is transmitted to the control unit of the pressure-guided bone cement injection system. The system adapts injection conditions based on differences in bone cement saturation within the vertebral bodies, overcoming issues such as blockage and leakage commonly associated with bone cement injection in existing technologies. This results in an effective enhancement of the injection efficiency and safety of bone cement injection.

SYMBOL EXPLANATION

Figure 1:
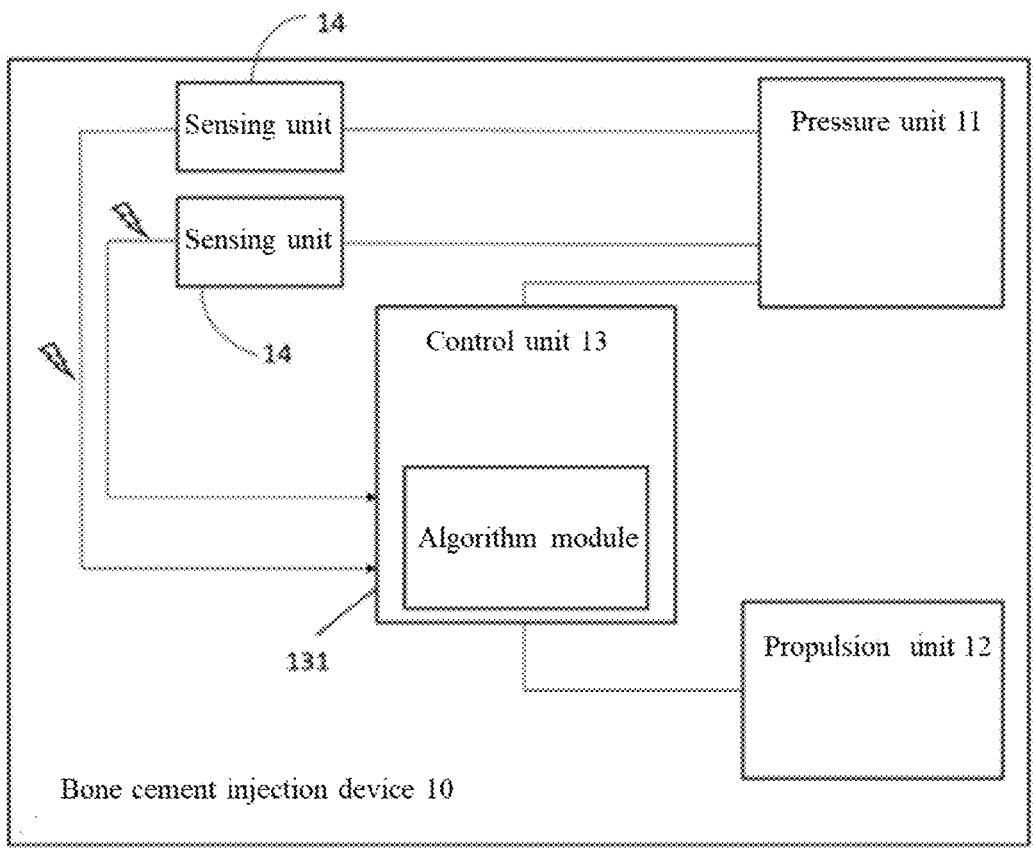
FIG. 1 A preferred embodiment of the pressure-guided bone cement injection device of the present invention, depicted as a system block diagram.
Figure 2:
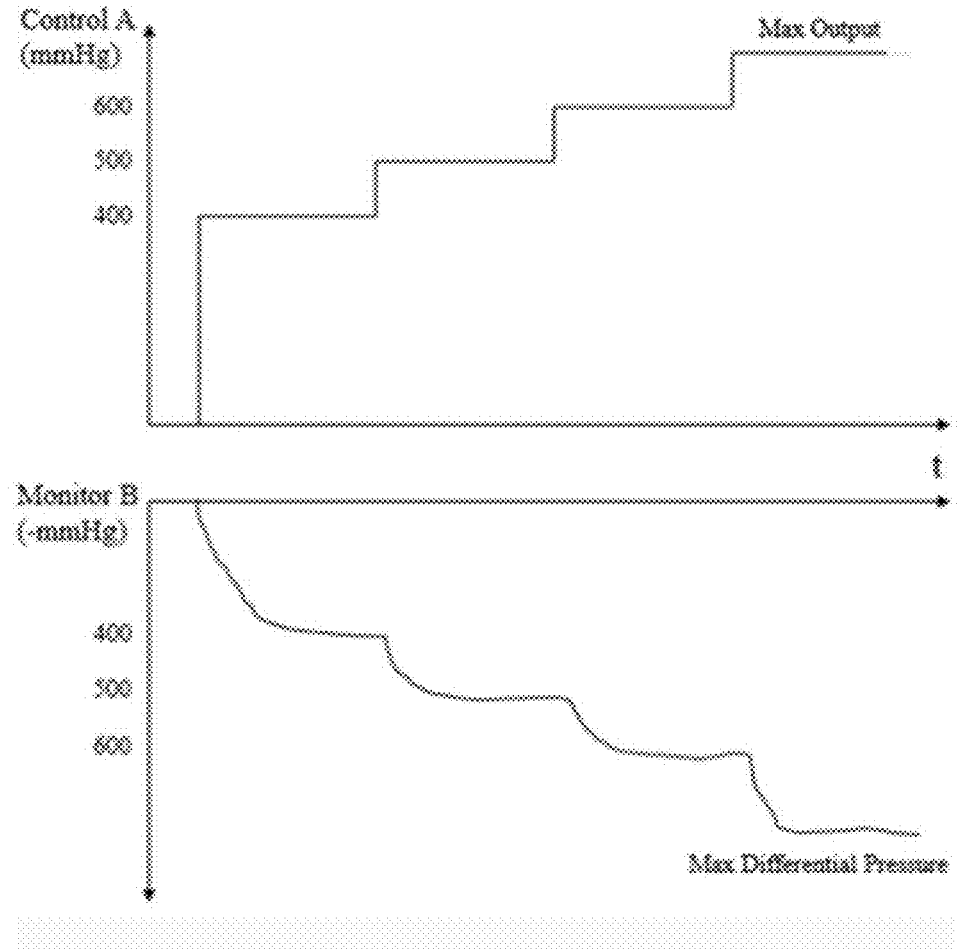
FIG. 2 A preferred embodiment of the system flowchart for the pressure-guided bone cement injection method of the present invention.
Figure 3:
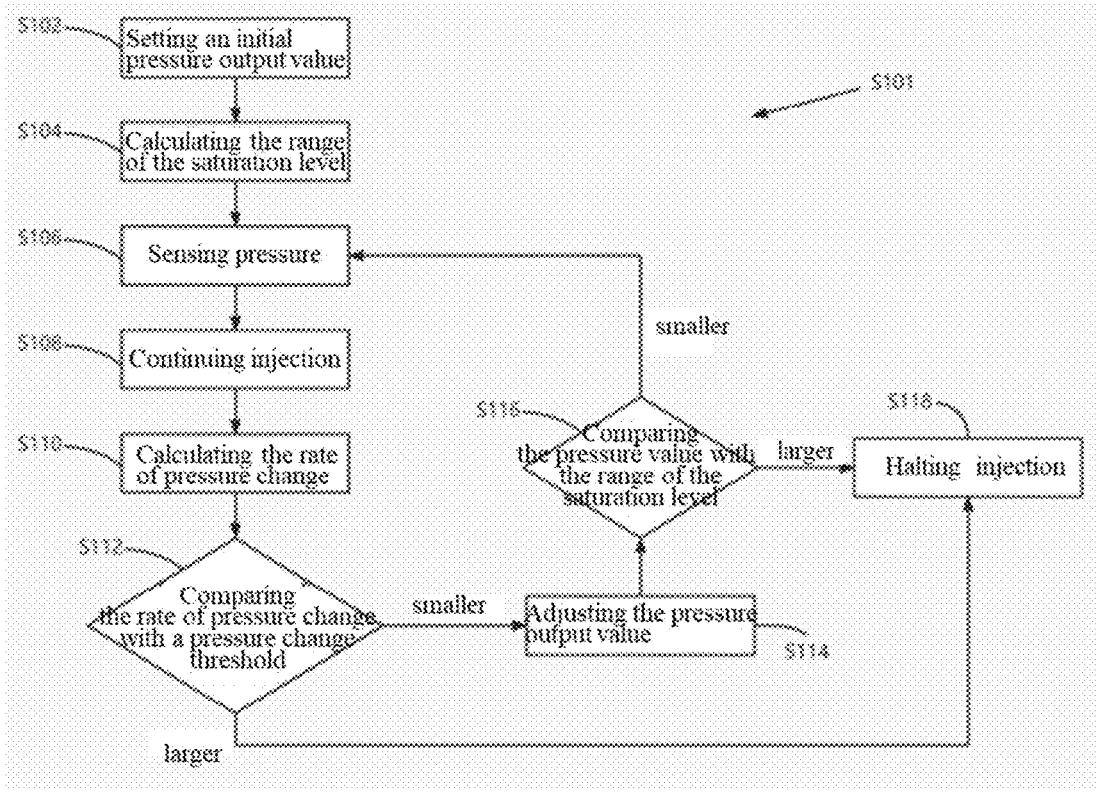
FIG. 3 An illustration of a preferred embodiment of the pressure-guided bone cement injection method of the present invention.

10 Pressure-guided bone cement injection device
11 Pressure unit

12 Propelling unit
13 Control unit
14 Sensing unit
101 Control algorithm
131 Algorithm module

DETAILED DESCRIPTION OF THE INVENTION

Hereafter, specific embodiments are provided as examples to elucidate the technical content, features, and achievements of the invention, and these examples can be used for implementation. However, it should be noted that the scope of protection of the present invention is not limited thereto.

Embodiment 1 Citation for Pressure-Guided Bone Cement Injection Device

The pressure-guided bone cement injection method of this embodiment requires the use of a pressure-guided bone cement injection device 10. The device provides a pressure pump as the source of pressure guidance, and this pressure pump is connected to a needle tube with an injection opening at the other end. Pressure is introduced into the target site through this needle tube. On the other hand, the bone cement injection pump is equipped with a regulating valve to control the positive pressure of the bone cement injection pump. The bone cement injection pump is also connected to a needle tube with an injection opening at the other end, allowing the bone cement to be introduced into the target site under the pressure provided by the bone cement injection pump.

In terms of the sensing unit 14, the pressure-guided bone cement injection device 10 is equipped with a pressure sensor to detect the pressure value at the target site. This allows for the assessment of the resistance status at the target site to adjust the pressure intensity or the injection rate of bone cement.

Furthermore, the control unit 13 in this embodiment contains an algorithm module 131 capable of recording and analyzing the pressure change signals from the target site and the bone cement injection device. It integrates relevant data to evaluate the bone cement injection pattern, adjust pressure intensity, and provide instructions or prompts to stop the bone cement injection based on the analyzed information.

Embodiment 2 Method of Operating Pressure-Guided Bone Cement Injection

Prior to activating the pressure-guided bone cement injection device 10 provided in Embodiment 1, the operator can determine the initial output pressure value of the pressure unit 11. After deciding the initial pressure output value, the control system 13 calculates the bone cement approaching saturation range. The pressure pump in the pressure unit 11 starts operating, and the pressure sensor measures a pressure value, which is then fed back to the algorithm for calculating the pressure change rate. The calculated rate is compared with the pressure change threshold. If the detected pressure change exceeds the threshold, a control signal is sent to stop the cement injection. If the detected pressure change is below the threshold, the pressure output value is increased until reaching the maximum pressure output value or approaching the saturation range of the bone cement. A control signal is then sent to stop the cement injection.

In this embodiment, the instruction to the pressure output device sets its initial pressure output value to 400 mmHg. When the pressure within the vertebral body cannot move the bone cement at 400 mmHg, the intermediate pressure value is increased to 500 mmHg. This process continues, gradually increasing the pressure output value until reaching the maximum output value, which in this example is 680 mmHg. The algorithm determines to stop the injection and issues a command to cease the bone cement injection.

Figure 4:
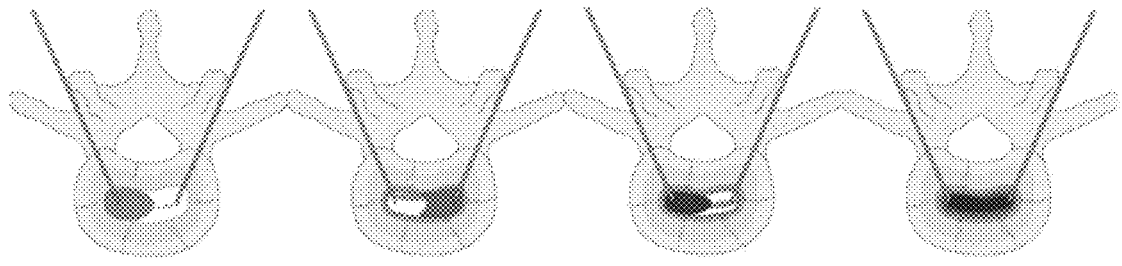
FIGS. 4 An illustration of a preferred embodiment of the pressure-guided bone cement injection method of the present invention.
Figure 5:
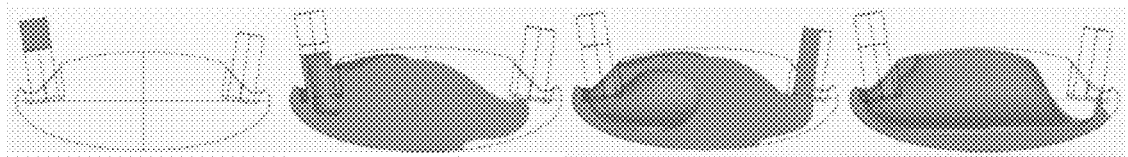
FIGS. 5 An illustration of a preferred embodiment of the pressure-guided bone cement injection method of the present invention.

In this embodiment, after a certain period, when the pressure change inside the target is detected to rise, the rotational speed of the pressure motor will gradually increase to enhance the provided pressure. In this example, the maximum output value is set at 680 mmHg. As shown in FIGS. 4 and 5, based on the principles described above, the pressure-guided bone cement injection method provided by the present invention, through pressure guidance, accelerates the process of bone cement being introduced into the affected area. Simultaneously, the bone cement continues to flow without stagnation, reducing the likelihood of solidification during the introduction process. By guiding the pressure, most of the bone cement is carried away from the vertebral body, leaving only a small amount on the inner wall of the vertebral body. This step allows the bone cement to slowly fill the vertebral body.

Figure 6:
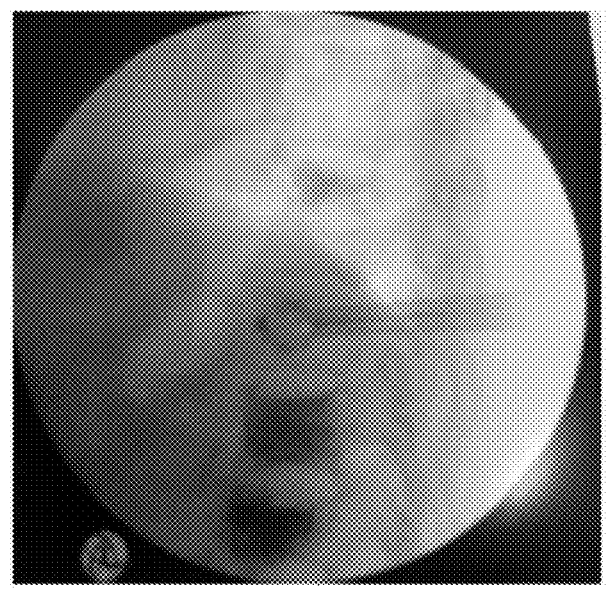
FIGS. 6 An illustration of a preferred embodiment of the pressure-guided bone cement injection system of the present invention.

Embodiment 3 Evaluation of Bone Cement Injection Efficiency in the Algorithm-Controlled Pressure-Guided Bone Cement Injection System The evaluation criteria for the effectiveness of bone cement injection in vertebral augmentation procedures or balloon kyphoplasty are illustrated in the X-ray image in FIG. 6, as shown in the invention diagram. FIG. 6 represents an X-ray image of the bone cement injection situation. In cases where the bone cement distribution is considered "excellent," as depicted in FIG. 6, a large amount of bone cement is observed in a flowing state being suctioned out under pressure shortly after the initiation of the cement injection. Only a small amount of bone cement remains, solidifying on the inner wall of the vertebral body.

The above-described embodiments are only exemplary embodiments of the present disclosure and are not intended to limit the scope of the present disclosure. All variations and modifications within the spirit and scope of the claims of the present application, including changes in shape, structure, features, and spirit, are encompassed within the scope of the patent claims of this application.

The invention claimed is:

1. A pressure-guided bone cement injection device, comprising:
   a pressure unit for introducing pressure;
   a propulsion unit for driving bone cement injection into a vertebral body;
   at least one sensing unit for detecting at least one environmental parameter; and
   a control unit connecting the pressure unit, the propulsion unit, and the sensing unit,
   wherein the environmental parameter comprises a monitored pressure value, wherein the control unit comprises an algorithm module,
   wherein the algorithm module is configured to perform the following steps:
   (a) setting an initial pressure output value;
   (b) receiving at least one environmental parameter sensed by the sensing unit;

(c) obtaining data through a computational process based on the at least one environmental parameter;

(d) continuing or halting the injection of bone cement and modifying the pressure output value of the pressure during continuing the injection of bone cement according to a data comparison process;

wherein the computational process includes defining a saturation range of bone cement within the vertebral body through subtracting the pressure output value from the pressure output value multiplied by a manually set parameter, calculating a pressure change rate using a differential or derivative method, and calculating a saturation level of bone cement through dividing the monitored pressure value by the pressure output value, wherein the data comparison process includes comparing the pressure change rate with a default pressure change threshold, and if the pressure change rate is less than the default pressure change threshold, commanding the control system to increase the pressure output value, then comparing the monitored pressure value with the saturation range of bone cement, and if the monitored pressure value is less than the saturation range of bone cement, commanding the sensing unit to re-monitor the monitored pressure value and repeating steps (a) to (d) until the monitored pressure value reaches a maximum output value, and if the pressure change rate exceeds the default pressure change threshold or the monitored pressure value exceeds the saturation range, commanding the propulsion unit to stop the injection of the bone cement.

2. A method for pressure-guided bone cement injection, comprising:

(a) setting an initial pressure output value;

(b) receiving at least one environmental parameter sensed by a sensing unit;

(c) obtaining data through a computational process based on the at least one environmental parameter;

(d) continuing or halting the injection of bone cement and adjusting the pressure output value of the pressure during continuing the injection of bone cement according to a data comparison process, wherein the computational process includes defining a saturation range of bone cement within the vertebral body through subtracting the pressure output value from the pressure output value multiplied by a manually set parameter, calculating a pressure change rate using a differential or derivative method, and calculating a saturation level of bone cement through dividing the monitored pressure value by the pressure output value, wherein the data comparison process includes comparing the pressure change rate with a default pressure change threshold, and if the pressure change rate is less than the default pressure change threshold, commanding the control system to increase the pressure output value, then comparing the monitored pressure value with the saturation range of bone cement, and if the monitored pressure value is less than the saturation range of bone cement, commanding the sensing unit to re-monitor the monitored pressure value and repeating steps (a) to (d) until the monitored pressure value reaches a maximum output value, and if the pressure change rate exceeds the default pressure change threshold or the monitored pressure value exceeds the saturation range, commanding the propulsion unit to stop the injection of the bone cement.

3. The method for pressure-guided bone cement injection according to claim 2, wherein the monitored pressure value comprises pressure value within the pressure introduction device, pressure value within the pressure unit, and pressure value within the vertebral body.

4. The method for pressure-guided bone cement injection according to claim 2, wherein the algorithm module determines that the pressure output value should not exceed the maximum pressure output value.

5. The method for pressure-guided bone cement injection according to claim 2, wherein the initial pressure output value is not allowed to be less than 0 mmHg.

* * * * *